US007585945B2

(12) United States Patent
Kim et al.

(10) Patent No.: US 7,585,945 B2
(45) Date of Patent: Sep. 8, 2009

(54) USE OF RECOMBINANT HEAT SHOCK PROTEIN COMPLEXED TO KIDNEY CANCER ANTIGEN

(75) Inventors: Hyung Kim, Amherst, NY (US); Xiang Wang, Buffalo, NY (US); Xiaolei Sun, Buffalo, NY (US); John Subjeck, Williamsville, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 11/894,970

(22) Filed: Aug. 22, 2007

(65) Prior Publication Data

US 2008/0085285 A1 Apr. 10, 2008

Related U.S. Application Data

(60) Provisional application No. 60/840,127, filed on Aug. 25, 2006.

(51) Int. Cl.
*C07K 1/00* (2006.01)
(52) U.S. Cl. .................................... 530/350
(58) Field of Classification Search ............... 530/350; 435/190
See application file for complete search history.

(56) References Cited

U.S. PATENT DOCUMENTS

| 2002/0039583 A1 | 4/2002 | Subjeck et al. ............ 424/185.1 |
| 2005/0202035 A1 | 9/2005 | Subjeck et al. ............ 424/185.1 |

FOREIGN PATENT DOCUMENTS

WO   2004/035785   *   4/2004

OTHER PUBLICATIONS

Lindquist, S. & Craig, E. A. The heat-shock proteins. Annu Rev Genet 22, 631-77 (1988).
Gething, M. J. & Sambrook, J. Protein folding in the cell. Nature 355, 33-45 (1992).
Knittler, M.R. & Haas, I.G., Interaction of BiP with Newly Synthesized Immunoglobulin Light Chain Molecules: Cycles of Sequential Binding and Release, EMBO Journal vol. 11 No. 4 p. 1573-1591, 1992.
Sciandra, J. J. & Subjeck, J. R. Heat shock proteins and protection of proliferation and translation in mammalian cells. Cancer Res 44, 5188-94 (1984).
Shen, J. et al. Coinduction of glucose-regulated proteins and doxorubicin resistance in Chinese hamster cells. Proc Natl Acad Sci U S A 84, 3278-82 (1987).
Srivastava, P. Roles of heat-shock proteins in innate and adaptive immunity. Nat Rev Immunol 2, 185-94 (2002).
Klein, G., Sjogren, H. O., Klein, E. & Hellstrom, K. E. Demonstration of resistance against methylcholanthrene-induced sarcomas in the primary autochthonous host. Cancer Res 20, 1561-72 (1960).

Udono, H. & Srivastava, P. K. Comparison of tumor-specific immunogenicities of stress-induced proteins gp96, hsp90, and hsp70. J Immunol 152, 5398-403 (1994).
Castelli, C. et al. Human heat shock protein 70 peptide complexes specifically activate antimelanoma T cells. Cancer Res 61, 222-7 (2001).
Todryk, S. M., Melcher, A. A., Dalgleish, A. G. & Vile, R. G. Heat shock proteins refine the danger theory. Immunology 99, 334-7 (2000).
Binder, R.J., Han, D. K. & Srivastava, P. K. CD91: a receptor for heat shock protein gp96. Nat Immunol 1, 151-5 (2000).
Basu, S., Binder, R. J., Ramalingam, T. & Srivastava, P. K. CD91 is a common receptor for heat shock proteins gp96, hsp90, hsp70, and calreticulin. Immunity 14, 303-13 (2001).
Asea, A. et al. HSP70 stimulates cytokine production through a CD14-dependant pathway, demonstrating its dual role as a chaperone and cytokine. Nat Med 6, 435-42 (2000).
Udono, H., Levey, D. L. & Srivastava, P. K. Cellular requirements for tumor-specific immunity elicited by heat shock proteins: tumor rejection antigen gp96 primes CD8+ T cells in vivo. Proc Natl Acad Sci U S A 91, 3077-81 (1994).
Matsutake, T. & Srivastava, P. K. The immunoprotective MHC II epitope of a chemically induced tumor harbors a unique mutation in a ribosomal protein. Proc Natl Acad Sci 98, 3992-7 (2001).
Basu, S., Binder, R. J., Suto, R., Anderson, K. M. & Srivastava, P. K. Necrotic but not apoptotic cell death releases heat shock proteins, which deliver a partial maturation signal to dendritic cells and activate the NF-kappa B pathway, Int Immunol 12, 1539-46 (2000).
Chen, W., Syldath, U., Bellmann, K., Burkart, V. & Kolb, H. Human 60-kDa heat-shock protein: a danger signal to the innate immune system. J Immunol 162, 3212-9 (1999).
Kol, A., Lichtman, A. H., Finberg, R. W., Libby, P. & Kurt-Jones, E. A. Cutting edge: heat shock protein (HSP) 60 activates the innate immune response: CD14 is an essential receptor for HSP60 activation of mononuclear cells. J Immunol 164, 13-7 (2000), Abstract.
Amato, R. et al. in ASCO A1782 (2000).
Assikis, V. J. et al. in ASCO A1552 (2003), Abstract.
Wood, C. et al. in ASCO A2618 (2004), Abstract.
Udono, H., Yamano, T., Kawabata, Y., Ueda, M. & Yui, K. Generation of cytotoxic T lymphocytes by MHC class I ligands fused to heat shock cognate protein 70. Int Immunol 13, 1233-42 (2001).
Suzue, K., Zhou, X., Eisen, H. N. & Young, R. A. Heat shock fusion proteins as vehicles for antigen delivery into the major histocompatibility complex class I presentation pathway. Proc Natl Acad Sci U S A 94, 13146-51 (1997).
Anthony, L. S. et al. Priming of CD8+ CTL effector cells in mice by immunization with a stress protein-influenza virus nucleoprotein fusion molecule. Vaccine 17, 373-83 (1999).
Manjili, M. H. et al. Cancer immunotherapy: stress proteins and hyperthermia. Int J Hyperthermia 18, 506-20 (2002).
Manjili, M. H. et al. Development of a recombinant HSP110-HER-2/neu vaccine using the chaperoning properties of HSP110. Cancer Res 62, 1737-42 (2002).

(Continued)

*Primary Examiner*—Maryam Monshipouri
(74) *Attorney, Agent, or Firm*—Michael L. Dunn

(57) ABSTRACT

A heat shock protein in combination with carbonic anhydrase IX and a method for improving immune response to carbonic anhydrase IX in a mammal by complexing it with a heat shock protein prior to administration to the mammal.

2 Claims, 5 Drawing Sheets

OTHER PUBLICATIONS

Wang, X. Y. et al. Targeted immunotherapy using reconstituted chaperone complexes of heat shock protein 110 and melanoma-associated antigen gp100. Cancer Res 63, 2553-60 (2003).

Binder, R. J., Anderson, K. M., Basu, S. & Srivastava, P. K. Cutting edge: heat shock protein gp96 induces maturation and migration of CD11c+ cells in vivo. J Immunol 165, 6029-35 (2000).

* cited by examiner

RT 45 55

HSP110

CA9

USE OF RECOMBINANT HEAT SHOCK PROTEIN COMPLEXED TO KIDNEY CANCER ANTIGEN

CROSS-REFERENCE TO RELATED APPLICATION

This application claims the benefit under 35 U.S.C. §119 (e) of U.S. Provisional Application No. 60/840,127, filed Aug. 25, 2006.

STATEMENT REGARDING FEDERALLY SPONSORED RESEARCH OR DEVELOPMENT

This work was supported by the Institutional ACS (USA) Grant IRG-02-197-01. The United States Government may have certain rights in this invention.

BACKGROUND OF THE INVENTION

The standard treatment for metastatic renal cell carcinoma (RCC) includes cytokine therapy with interferon-alpha (IFN-α) or interleukin-2 (IL2), which produce 15-20% response rates. These modest response rates highlight the need for more effective treatments; however, they also indicate that RCC is immunoresponsive. An effective tumor vaccine targets antigens that are highly expressed on tumor cells. Recombinant heat shock proteins (HSP) can be used to stimulate the immune system to target tumor-specific antigens, leading to tumor killing. HSP are one of the most abundant proteins found inside a cell. They have the ability to bind and protect intracellular proteins in the presence of cellular stress, such as heat and glucose depravation.

Recombinant HSP, such as hsp100 and grp170, can be complexed to a tumor-specific antigen. Depending on the tumor antigen, the HSP-target antigen complex forms at room temperature or when heated. The complex is then administered as a vaccine that targets the tumor.

Heat shock proteins (HSP) are some of the most abundant intracellular proteins. They normally function as molecular chaperones, assisting with protein folding and formation of multi-subunit complexes. They are induced by cellular stress and protect intracellular proteins by binding and preventing denaturation. HSP are broadly categorized as hsps (designated here using small characters) or glucose regulated proteins (grps) based on their subcellular localization and the stressors that induce their expression ((Shen, J. et al., Coinduction of glucose-regulated proteins and doxorubicin resistance in Chinese hamster cells. Proc Natl Acad Sci USA 84, 3278-82 (1987)) ((Srivastava, P., Roles of heat-shock proteins in innate and adaptive immunity. Nat Rev Immunol 2, 185-94 (2002)). For example, hsps (families of hsps: small hsps, hsp40, calreticulin, hsp60, hsp70, hsp90, hsp110) are induced by heat and oxidizing agents, and localize to the nucleus, cytoplasm and mitochondria. Grps (family of grps: grp78, grp94, grp170) are induced by hypoxia and glucose deprivation, and localize to the endoplasmic reticulum.

Experiments performed in the early 1900s demonstrated that tumor cells and lysates can protect mice against subsequent tumor challenges. Follow up experiments using tumor fractions identified HSP as the "active ingredient" providing immune protection (Udono, H. & Srivastava, P. K., Comparison of tumor-specific immunogenicities of stress-induced proteins gp96, hsp90, and hsp70. J Immunol 152, 5398-403 (1994)). The HSP may be promiscuously bound to a number of tumor antigens, which may produce a tumor-specific immune response; although, it is not yet possible to specifically predict with any certainty that that such a response will in fact occur with a particular HSP bound to a particular antigen without actual tests (Castelli, C. et al. Human heat shock protein 70 peptide complexes specifically activate anti-melanoma T cells. Cancer Res 61, 222-7 (2001)).

It has been postulated that HSP found outside a cell are recognized as a danger signal, indicating to the immune system the presence of damaged or diseased tissue. Receptors for HSP have been identified on dendritic cells (DC), which are professional antigen presenting cells (APC). Using solubilized APC membrane applied to a gp96 affinity column, CD91 was identified as a receptor for HSP; CD91 binds hsp90, hsp70 and calreticulin. Various scavenger receptors including CD14, TLR-2 and TLR4 have been shown to bind and internalize hsp70 and hsp60. The binding of HSP and DC leads to NF-κB signaling, which has previously been shown to regulate cytokines and DC maturation.

In certain cases, microgram quantities of HSP bound to peptides may serve as a powerful immune adjuvant, activating both an antigen-specific and an innate immune response. While the majority of exogenous antigens produce a MHC class II response, proteins and peptides bound to HSP may elicit a MHC class I mediated CD8+ T cell response as well as a MHC class II response (Udono, H., Levey, D. L. & Srivastava, P. K., Cellular requirements for tumor-specific immunity elicited by heat shock proteins: tumor rejection antigen gp96 primes CD8+ T cells in vivo. Proc Natl Acad Sci USA 91, 3077-81 (1994)) (Matsutake, T. & Srivastava, P. K., The immunoprotective MHC II epitope of a chemically induced tumor harbors a unique mutation in a ribosomal protein. Proc Natl Acad Sci USA 98, 3992-7 (2001)). The mechanism of cross presentation is the subject of active research; however, it known that cross presentation of peptides bound to HSP requires functional proteosomes and transporter associated with antigen processing (TAP). HSP uncomplexed to peptide might stimulate an innate immune response by stimulating the secretion of various cytokines including, TNFα, IL-1α, IL-6, IL-12, and GM-CSF (Basu, S., Binder, R. J., Suto, R., Anderson, K. M. & Srivastava, P. K., Necrotic but not apoptotic cell death releases heat shock proteins, which deliver a partial maturation signal to dendritic cells and activate the NF-kappa B pathway. Int Immunol 12, 1539-46 (2000).) (Kol, A., Lichtman, A. H., Finberg, R. W., Libby, P. & Kurt-Jones, E. A., Cutting edge: heat shock protein (HSP) 60 activates the innate immune response: CD14 is an essential receptor for HSP60 activation of mononuclear cells. J Immunol 164, 13-7 (2000)). Both the antigen-specific and the innate immune responses contribute to the final anti-tumor effect.

HSP vaccine strategies have been reported by others. HSPs are complexed to a wide spectrum of intracellular tumor proteins. It is therefore possible to isolate these HSPs and administer them as a tumor-specific, autologous vaccine. In principle, this approach is similar to using tumor lysate as a vaccine; however, the extraction of tumor HSPs produces a more concentrated vaccine enriched for the "active ingredient". Using this approach, a phase III clinical trial for metastatic melanoma and a phase III adjuvant therapy trial for kidney cancer have completed enrollment. In two different phase II trials for metastatic kidney cancer, approximately 35% of patients had a clinical response. No significant toxicities were observed, and no autoimmune effects were noted (Amato, R. et al. in ASCO A1782 (2000)) (Assikis, V. J. et al. in ASCO A1552 (2003)).

There unfortunately are limitations to using tumor derived HSPs. Surgically obtained tumor tissue is not available for all patients. Even when tumor tissue is available, a vaccine can not be prepared in approximately 10% of cases. Finally, only a small fraction of relevant tumor peptides in the vaccine produce an antitumor effect. Therefore, in an effort to produce a highly concentrated vaccine against a known tumor antigen, genetically engineered proteins consisting of HSP fused to the C or N terminus of a tumor protein were synthesized (Udono, H., Yamano, T., Kawabata, Y., Ueda, M. & Yui, K., Generation of cytotoxic T lymphocytes by MHC class I ligands fused to heat shock cognate protein 70. Int Immunol 13, 1233-42 (2001)) (Suzue, K., Zhou, X., Eisen, H. N. & Young, R. A., Heat shock fusion proteins as vehicles for antigen delivery into the major histocompatibility complex class I presentation pathway. Proc Natl Acad Sci U S A 94, 13146-51 (1997)) (Anthony, L. S. et al., Priming of CD8+ CTL effector cells in mice by immunization with a stress protein-influenza virus nucleoprotein fusion molecule. Vaccine 17, 373-83 (1999)). In most cases the HSP is of microbial origin and can itself produce an immune response. Although an unlimited supply of vaccine can be produced, this approach does not produce an immune response in all cases. A HPV 16-E7 (cervical cancer antigen)-hsp110 fusion vaccine was, for example, created that did not produce a CD8+ CTL response in vivo (unpublished data). A possible explanation for this negative result is that a fusion protein is an unnatural construct and interactions with APC depend on proper positioning and steric changes associated with noncovalent complexing of HSP and tumor antigen.

BRIEF DESCRIPTION OF THE INVENTION

Carbonic anhydrase IX (CA9) has been identified recently as a potential target for immunotherapy. CA9 is present in 95-100% of clear renal carcinoma cells (RCC) and it is not present in normal, nonmucosal tissue. We have now found that HSP proteins, normally found inside a cell, are powerful immune activators when found outside a cell that are capable of stimulating an immune response against proteins complexed to the HSP.

DETAILED DESCRIPTION OF THE INVENTION

We have now demonstrated in an animal model that recombinant CA9 complexed to HSP can serve as an effective RCC vaccine.

Figure 1:
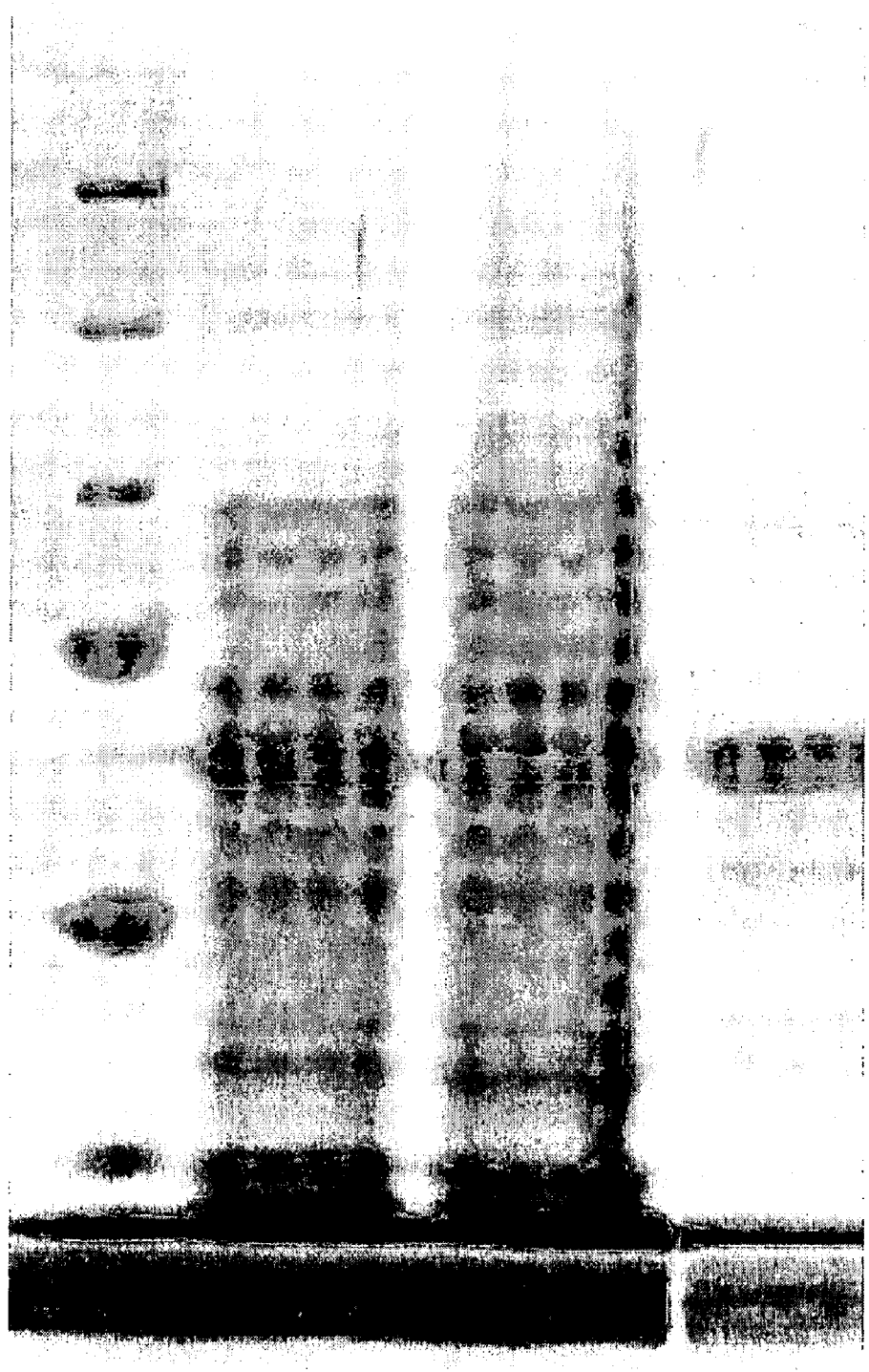
FIG. 1 shows a Coomassie blue-gel staining of whole cell lysate (center 2 lanes) and purified recombinant CA9 (right lane). CA9 cDNA was subcloned into the pRSETA vector. The plasmid was transformed into *Escherichia coli* cells and the protein was purified using a nickel nitriloacetic acid-agarose column.

As an example, in accordance with the invention, mouse hsp110 was cloned into pBacPAK-his vector (BD Biosciences Clontech, Palo Alto, Calif.) and expressed using a BacPAK baculovirus system using methods known to those skilled in the art. A known CA9 cDNA in accordance with the present invention was subcloned into the pRSETA vector (Invitrogen, Carlsbad, Calif.). The plasmid was transformed into *Escherichia coli* JM109 (DE3) cells and protein was purified (FIG. 1) using a nickel nitriloacetic acid-agarose column (Qiagen, Valencia, Calif.). Renal carcinoma (RENCA) cells, which are syngeneic with BALB/c mice, are used for the murine studies. RENCA does not normally express CA9, thus RENCA cells stably transduced by known methods to express human CA9 (RENCA-CA9) were obtained and used.

Figure 2:
FIG. 2 is a gel showing that HSP binds CA9 at 45° and 55° C., but not at room temperature (RT). The hsp110-CA9 complex was immunoprecipitated using anti-hsp110 antibody. After SDS-PAGE (10%) electrophoresis, a western blot analysis was performed using anti-His antibody.
Figure 2:
Figure 3:
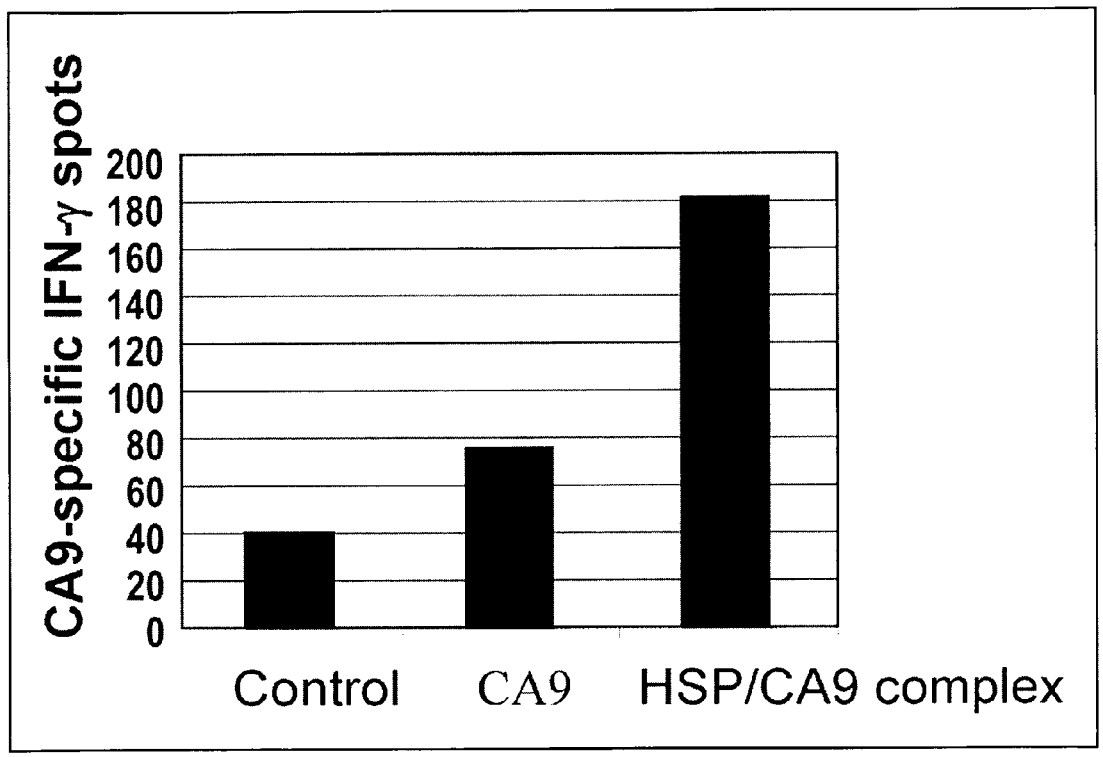
FIG. 3 is a bar graph showing that immunization with hsp110-CA9 complex elicits CA9-specific immune responses measured using an ELISPOT assay. Balb/c mice (3 mice/group) were immunized intradermally (i.d.) with PBS, CA9, or hsp110-CA9 complex. The splenocytes were harvested 10 d after 2 immunizations performed 10 days apart. IFN-γ spots were counted using the KS Elispot System (version 4.3.56) from Zeiss Microscopy.
Figure 4:
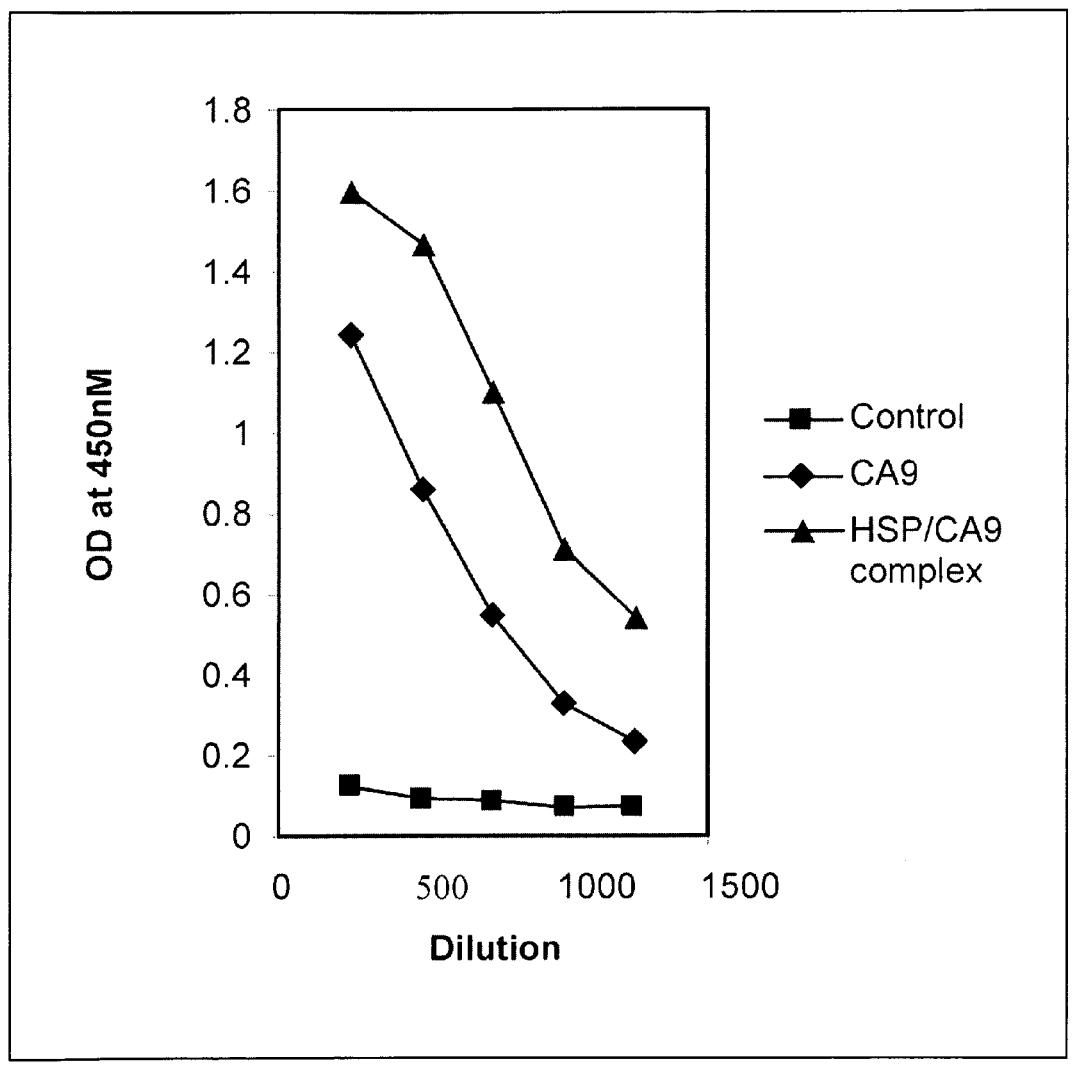
FIG. 4 is a line graph showing that immunization with hsp110-CA9 complex elicits CA9-specific humoral response measured using ELISA. Balb/c mice (3 mice/group) were immunized intradermally (i.d.) with PBS, CA9, or hsp110-CA9 complex. Five-fold serial dilutions of blood were tested for CA9 specific antibodies using CA9 coated microtiter plates (10 µg/ml).
Figure 5A:
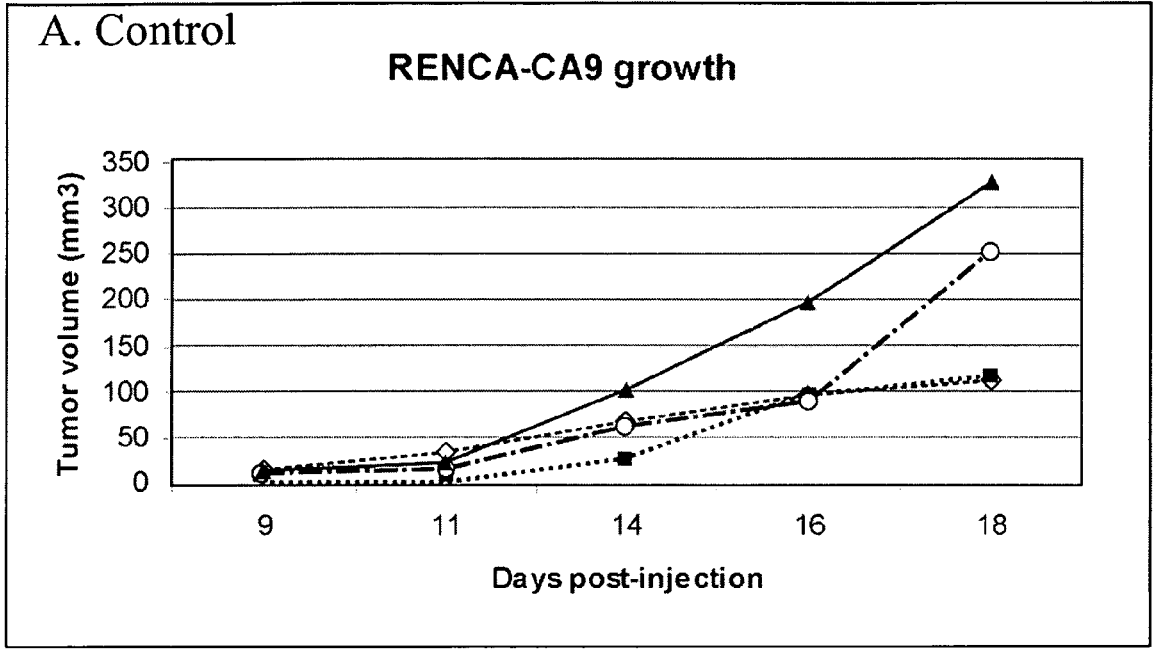
FIG. 5A. is a graph showing essentially no antitumor effect when $2 \times 10^5$ RENCA-CA9 tumor cells were injected subcutaneously 7 days after 3 immunizations with PBS administered 14 days apart (control; A)
Figure 5B:
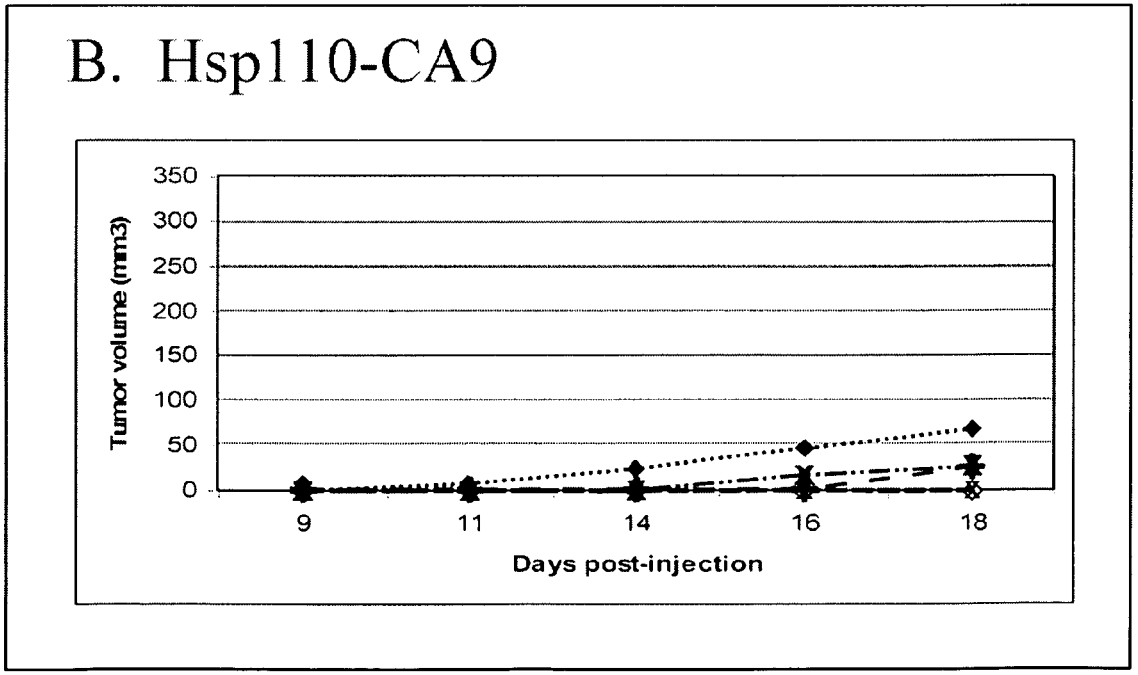
FIG. 5B is a graph showing significant antitumor effect when $2 \times 10^5$ RENCA-CA9 tumor cells were injected subcutaneously 7 days after 3 immunizations with hsp110-CA9 (B) administered 14 days apart. Each line represents tumor growth in a single mouse. Immunization with hsp110-CA9 has an antitumor effect.

Preliminary data from our laboratory demonstrates that a HSP based vaccine can produce a CA9 specific immune response in vivo. HSP is capable of binding partially denatured protein, and preventing further protein denaturation and aggregation. It is possible to take advantage of this feature by heat shock complexing HSP and CA9 in vitro (FIG. 2). This complex can then be administered as a vaccine. In a mouse model, the HSP/CA9 complex administered intradermally (i.d.) led to cross presentation and generated a CA9 specific cytotoxic T-lymphocyte (CTL) response measured using an Elispot assay (FIG. 3). Vaccination with HSP/CA9 complex also produced a humoral response and generated CA9 specific antibodies (FIG. 4). Our data demonstrates that vaccination with HSP/CA9 complex in a murine model produces an antitumor effect (FIG. 5).

The vaccine strategy described here takes advantage of the in vivo function of HSP for use in a kidney cancer vaccine, and was first proposed by John Subjeck's group (Manjili, M. H. et al., Cancer immunotherapy: stress proteins and hyperthermia. Int J Hyperthermia 18, 506-20 (2002)) (Manjili, M. H. et al., Development of a recombinant HSP110-HER-2/neu vaccine using the chaperoning properties of HSP110. Cancer Res 62, 1737-42 (2002)) (Wang, X. Y. et al., Targeted immunotherapy using reconstituted chaperone complexes of heat shock protein 110 and melanoma-associated antigen gp100. Cancer Res 63, 2553-60 (2003)). Recombinant HSP and a target tumor protein/antigen can be combined at room temperature or heat shocked in vitro to produce a noncovalent complex. The temperature (amount of heat) necessary for forming a "chaperone complex" of HSP110 with a protein antigen depends on the antigen. Different antigens/proteins have different melting temperatures. This complex provides the same danger signal provided by intracellular HSP released in various disease states associated with cellular damage. Advantages include the following:

1) This preparation is a highly concentrated vaccine directed at a known tumor target.
2) This preparation can be produced in unlimited quantity.
3) This preparation has the potential to be effective against all tumors expressing the target.
4) If the full length protein is used, the vaccine can be used in all patients, regardless of HLA restrictions.
5) There are currently no immune adjuvants approved for human use that are effective in stimulating a cell-mediate immune response. The only immune adjuvants currently approved for human use are aluminum, calcium phosphate, and a squalene formulation, which effectively stimulate a humoral response, but are poor stimulants of a cellular response (Binder, R. J., Anderson, K. M., Basu, S. & Srivastava, P. K., Cutting edge: heat shock protein gp96 induces maturation and migration of CD11c+ cells in vivo. J Immunol 165, 6029-35 (2000)).

The following specific examples serve to illustrate and not limit the present invention:

Mice and Cell Lines 6-8 week old female BALB/c mice were purchased from the NCI (Frederick, Md.) and housed under pathogen-free conditions. Parental RENCA cells and RENCA cells stably transduced to express human CA9 (RENCA-CA9) were provided by Dr. Arie Belldegrun (University of California, Los Angeles). CA9 expression in RENCA-CA9 was confirmed using western blot and monoclonal antibody against CA9, obtained from Dr. Egbert Oosterwijk (University Hospital of Nijmegen, Nijmegen, Netherlands). The RENCA lines were maintained in RPMI 1640, 10% heat-inactivated fetal calf serum, 1% glutamine, 1% nonessential amino acids, 1% sodium pyruvate, 1% penicillin/streptomycin, and 1% HEPES buffer.

Expression and Purification of Recombinant Proteins

Mouse Hsp110 and human CA9 cDNA (obtained from Dr. Belldegrun) were cloned into pBacPAK-his vector (BD Biosciences Clontech, Palo Alto, Calif.), transformed into monolayer Sf21 cells using replication defective virus, and expressed using the BacPAK baculovirus system. Proteins were purified using a nickel nitriloacetic acid-agarose column (Qiagen, Valencia, Calif.). Protein concentrations were measured using a Protein Assay Kit (Bio-Rad, Hercules, Calif.). Protein purity was assessed using sodium dodecyl sulfate-polyacrylamide gel electrophoresis and Coomassie Blue staining. Endotoxin levels in recombinant proteins were assessed using a Limulus Amebocyte lysate kit (Biowhittaker, Walkersville, Md.) and noted to be 10-25 endotoxin units/ng protein.

Reconstitution of Heat Shock Protein and Antigen Complex

Recombinant hsp110 and CA9 were complexed at 1:1 molar ratio and incubated for 30 minutes at room temperature (RT) or at heat shock temperatures of 45 or 55 degrees Celsius. It is understood that similar results can be obtained at comparable molar ratios, e.g. about 0.8:1 to about 1:0.8. The complex was immunoprecipitated using anti-hsp110 antibody to verify noncovalent binding between hsp110 and CA9. After SDS-PAGE (10%) electrophoresis, western blot analysis was performed using anti-His antibody (Amersham, Piscataway, N.J.). For the in vivo studies, hsp110 and CA9 were complexed at RT. CA9 peptide (A Y E Q L L S R L) was ordered from Alpha Diagnostics (San Antonio, Tex.) and similarly complexed to hsp110.

Construction of DNA Vaccine

A DNA vaccine consisting of pcDNA3.1 vector (Invitrogen, Carlsbad, Calif.) carrying CA9 fused to the N terminus of grp170 was constructed. Control vaccines included pcDNA3.1 carrying CA9 alone or grp170 alone. All genes were inserted behind a CMV promoter and sequence was verified. Protein expression was verified in transfected COS cells.

Tumor Prevention Study

For the tumor prevention studies, mice (5 per group) were immunized 3 times, 14 days apart, with 100 µl of vaccine. 7 days after the last immunization, 2×105 RENCA-CA9 cells were injected intradermally. Tumor growth ((shortest diameter2×longest diameter)/2) was monitored every 2 days using an electronic caliper. The complete set of experiments was repeated 3 times. The vaccination groups for the protein vaccines included PBS (control), CA9 (25 µg) alone, hsp110 (50 µg) alone, CA9 (25 µg)+50 µl Freud's Adjuvant (CA9+FA), and hsp110 complexed to CA9 (hsp110+CA9; 75 µg). The vaccination groups for the CA9 peptide-based vaccines included PBS (control), CA9 peptide (50 µg), hsp110 complexed to CA9 peptide (hsp110+CA9 peptide; 100 µg). The vaccination groups for the DNA vaccine included pcDNA3.1 carrying CA9 (10 µg) alone, grp170 (10 µg) alone, and CA9-grp170 (10 µg). CA9+FA vaccine was injected subcutaneously and all other vaccines were injected intradermally.

Tumor Treatment Study

This study was similar to the tumor prevention assay except that mice were injected intradermally with 2×105 RENCA-CA9 cells and after tumor implantation the vaccines were injected on days 3, 9, and 14 after tumor implantation. Tumor growth was monitored as previously described.

ELISPOT

Splenocytes were harvested 2 weeks after immunization and stimulated in vitro with irradiated RENCA-CA9 for 5 days. Filtration plates (Millipore, Bedford, Mass.) were coated with 10 µg/ml rat antimouse IFN-γ (clone R4-6A2; PharMingen, San Diego, Calif.) at 4° C. overnight, washed and blocked. Splenocytes (5×105/well) were incubated with CA9 (20 µg/ml) at 37° C. for 24 hours, then washed. A biotinylated IFN-γ antibody (5 µg/ml; clone XMG1.2; PharMingen), avidin-alkaline phosphatase D (0.2 unit/ml; Vector Labs, Burlingame, Calif.) and 5-bromo-4-chloro-3-indolyl phosphate/nitroblue tetrazolium (Boehringer Mannheim, Indianapolis, Ind.) were used to detect IFN-γ secretion. IFN-γ spots were counted using the KS Elispot System (version 4.3.56) from Zeiss Microscopy.

ELISA

Five-fold serial dilutions starting at 1:200 of serial bleedings from immunized mice were tested for CA9-specific antibodies using CA9 coated microtiter plates (10 µg/ml). Antibodies were detected using biotinylated anti-mouse IgG1 or IgG2a, avidin-alkaline phosphatase D (0.2 unit/ml; Vector Labs) and 5-bromo-4-chloro-3-indolyl phosphate/nitroblue tetrazolium (Boehringer Mannheim). Binding specificity was assessed by testing the sera using a control protein coated on the microtiter plates and by testing preimmune sera. Optical densities (OD) were read at 450 nm in a Titertek Multiscan MCC/340 plate scanner. For ELISA assays, the OD at 450 nm and 1:200 dilution is reported.

Statistical Analysis

Differences in tumor growth were assessed by repeating measure ANOVA. A p-value <0.05 was considered significant. All statistical analysis was performed using Stata 8.0 (College Station, Tex.).

Results

Hsp110 binds CA9 in vitro. Recombinant hsp110 and CA9 were combined at 1:1 molar ratio and noncovalent binding was confirmed by immunoprecipitating the complex using anti-hsp110 antibody (FIG. 2). After SDS-PAGE (10%) electrophoresis, western blot analysis was performed using anti- His antibody. HSP binds CA9 at room temperature, and binding increases at 45° and 55° C.

Hsp110+CA9 was evaluated as a tumor vaccine in a RENCA murine model. In a tumor prevention assay, BALB/c mice were immunized prior to injection of RENCA-CA9. Hsp110+CA9 prevented tumor growth in all animals. Although both CA9 alone and hsp110 alone decreased tumor growth, the effect was not statistically significant when compared to the control group that was immunized with PBS. When the mice challenged with RENCA-CA9 were observed for 40 days, none of the mice immunized with hsp110+CA9 developed tumors (FIG. 3). At 40 days, one of 5 mice immunized with hsp110 was tumor free. All other mice developed palpable tumors at the site of tumor injection.

Immunization with hsp110+CA9 produced both cellular and humoral immune responses. Hsp110+CA9 generated a CA9-specific cytotoxic T-lymphocyte (CTL) response measured using Elispot assay. CA9 alone and CA9 with complete FA produced lesser CTL responses. Vaccination with hsp110+CA9 also produced CA9 specific antibodies as measured by Elisa assay (FIG. 4b).

Alternative heat shock protein based tumor vaccine targeting CA9 were evaluated. A vaccine consisting of hsp110 complexed to an immunodominant CA9 peptide decreased growth of RENCA-CA9 in a tumor prevention assay. Hsp110+CA9 peptide vaccination generated CA9 specific CTLs, but produced no CA9 specific antibodies. A DNA vaccine consisting of pcDNA3.1 vector carrying CA9 fused to the N terminus of grp170 produced no antitumor effects in a tumor prevention assay. The vaccine produced no CA9 specific CTLs or CA9 specific antibodies.

Hsp110+CA9 is effective against established RENCA tumors. Of the 3 vaccine strategies evaluated, a complex of recombinant hsp110 and CA9 produced the most effect antitumor effect. Therefore, the vaccine employing full length proteins was evaluated in a tumor treatment assay. Balb/c mice were first injected intradermally with RENCA-CA9 to establish palpable tumors prior to treatment. Immunization with hsp110+CA9 significantly decreased tumor growth when compared to immunization with PBS. CA9 alone decreased tumor growth; however, the difference when compared to the PBS control did not reach statistical significance.

The most common histologic subtype of RCC is the clear cell variant. Von Hippel-Lindau (VHL) mutations and deletions are found in over 50% of sporadic clear cell RCCs.(18, 19) Hypermethylation represents an additional mechanism for VHL inactivation(19, 20). In clear cell RCC the overexpression of CA9 is the direct consequence of the defect in VHL function, which normally functions to degrade and suppress HIF-1α. CA9 expression is positively regulated by HIF-1α. Therefore, in the majority of clear cell RCCs, both HIF-1α and CA9 are constitutively expressed and no longer regulated by oxygen tension. CA9 expression is found in 95% of clear cell renal tumors with no expression in normal kidney. Expression in other normal tissue is limited to basal cells of hair follicles, gonadal epithelium, choroid plexus, and some gastrointestinal mucosa HSPs normally function as molecular chaperones, assisting with protein folding and formation of multi-subunit complexes. Experiments performed in the early 1900s demonstrated that tumor cells and lysates can protect mice against subsequent tumor challenges. Followup experiments using tumor fractions identified HSPs as the "active ingredient" providing immune protection. The HSPs are promiscuously bound to a large repertoire of tumor antigens, which produces a tumor-specific immune response. It is therefore possible to isolate these HSPs and administer them as a tumor-specific, autologous vaccine. Using this approach, a phase III clinical trial for metastatic melanoma and a phase III adjuvant therapy trial for kidney cancer have completed enrollment. In two different phase II trials for metastatic kidney cancer, approximately 35% of patients had a clinical response. No significant toxicities were observed, and no autoimmune effects were noted.

There are limitations to using tumor derived HSPs. Surgically obtained tumor tissue is not available for all patients. Even when tumor tissue is available, a vaccine can not be prepared in approximately 10% of cases. Finally, only a small fraction of relevant tumor peptides in the vaccine produce an antitumor effect. Recombinant HSP and a target tumor protein can be combined in vitro to produce a noncovalent complex. This complex provides the same danger signal provided by intracellular HSPs released in various disease states associated with cellular damage. Advantages to this approach include the following:

1) This preparation is a highly concentrated vaccine directed at a known tumor target.
2) This preparation is produced in unlimited quantity.
3) Although this vaccine would not be patient specific, it has the potential to be effective against all tumors expressing the target.
4) By using the full length protein, the vaccine can be used in all patients, regardless of HLA restrictions.

In this study, three HSP based tumor vaccines targeting CA9 were evaluated. All three strategies were screening using an in vivo tumor prevention model where vaccination was followed by tumor challenge. A vaccine using full-length, recombinant CA9 and hsp110 was most effect in preventing tumor growth, and produced robust cellular and humoral immune responses. A vaccine combining hsp110 and an immunodominant CA9 peptide also prevented tumor growth. As expected, a peptide based vaccine produced a cellular response but no humoral response. More effective antitumor effects may be possible with use of additional immunodominant peptides.

The final vaccine strategy evaluated was a DNA vaccine. A DNA vaccine obviates the technical challenges associated with production of recombinant proteins. However, a plasmid vector designed to express grp170 linked to CA9 had no antitumor effects and failed to produce a cellular or humor immune response. In unpublished work from our laboratory, a plasmid vector linking hsp110 and HPV 16-E7 was not effective as a tumor vaccine in a murine, cervical cancer model. Therefore, in the present study, a plasmid containing grp170 was constructed. Both large members of the hsp70 superfamily failed to produce an immune response against the linked antigen. A possible explanation is that a fusion protein is an unnatural construct and interactions with APCs depend on proper positioning and steric changes associated with noncovalent complexing of HSP and tumor antigen.

A tumor prevention model is analogous to the clinical setting in which adjuvant therapy is utilized. Adjuvant therapy is provided to patients at high risk for recurrence following resection of clinically localized RCC. These patients have no radiographically detectable disease following surgery, and the goal of adjuvant therapy is to prevent disease recurrence. This study suggests that a HSP based tumor vaccine targeting CA9 may be an effective adjuvant therapy. This vaccine strategy may also be effective in the treatment of metastatic RCC. To explore this possibility, the vaccine strategy shown to be most effective in the tumor prevention model was tested in a tumor treatment model where vaccine was administered after palpable, intradermal tumors were established. The recombinant protein vaccine combining hsp110 and CA9 was effective in decreasing the growth of established tumor.

In an animal model, recombinant hsp110 complexed to CA9 is an effective treatment for RCC, and produces a more effective antitumor effect than HSP-based strategies utilizing CA9 peptide or plasmid construct.

What is claimed is:

1. A composition comprising a mammalian recombinant heat shock protein hsp110 complexed with a carbonic anhydrase IX selected from the group consisting of a recombinant CA9 and an immunodominant CA9 where the CA9 has a human sequence.

2. The composition of claim 1 where the heat shock protein and the carbonic anhydrase IX are combined at a molar ratio of from about 0.8:1 to 1:0.8.

* * * * *